US007588764B2

(12) United States Patent
Nath et al.

(10) Patent No.: US 7,588,764 B2
(45) Date of Patent: Sep. 15, 2009

(54) COMPOSITIONS COMPRISING HUMAN IMMUNODEFICIENCY VIRUS TAT ADSORBED TO THE SURFACE OF ANIONIC NANOPARTICLES

(75) Inventors: Avindra Nath, Ellicott City, MD (US); Russell J. Mumper, Lexington, KY (US); Jerold Woodward, Lexington, KY (US); Zhengrong Cui, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 547 days.

(21) Appl. No.: 10/506,408

(22) PCT Filed: Feb. 27, 2003

(86) PCT No.: PCT/US03/05806

§ 371 (c)(1),
(2), (4) Date: Jun. 22, 2005

(87) PCT Pub. No.: WO03/073984

PCT Pub. Date: Sep. 12, 2003

(65) Prior Publication Data

US 2006/0051360 A1 Mar. 9, 2006

Related U.S. Application Data

(60) Provisional application No. 60/361,043, filed on Mar. 1, 2002.

(51) Int. Cl.
*A61K 39/21* (2006.01)
*A61K 39/385* (2006.01)
*A61K 45/00* (2006.01)

(52) U.S. Cl. .............. 424/188.1; 424/193.1; 424/208.1; 424/278.1

(58) Field of Classification Search ............... 424/208.1
See application file for complete search history.

(56) References Cited

U.S. PATENT DOCUMENTS 5,597,895 A * 1/1997 Gaynor et al. .............. 530/324
6,132,721 A 10/2000 Zagury et al.

OTHER PUBLICATIONS

Buanec, H. L., et al., 2001, Induction in mice of anti-Tat mucosal immunity by the intranasal and oral routes, Biomed. Pharmacother. 55:316-320.*
Cui, Z., and R. J. Mumper, 2002, Coating of cationized protein on engeineered nanoparticles results in enhanced immune responses, Intl. J. Pharmaeutics 238:229-239.*

Vives, E., et al., 1994, Effects of the Tat basic domain on human immunodeficiency virus type 1 transactivation, using chemically synthesized Tat protein and Tat peptides, J. Virol. 68(5):3343-3353.*

Rossi, C., et al., 1997, Inhibition of HIV-1 replication by a Tat transdominant negative mutant in human peripheral blood lymphocytes from healthy donors and HIV-1-infected patients, Gene Therapy 4:1261-1269.*

Pantaleo, G., and R. Koup, 2004, Correlates of immune protection in HIV-1 infection: what we know, what we don't know, what we should know, Nat. Med. 10(8):806-810.*

Gallo, R. C., 2005, The end or the beginning of the drive to an HIV-preventive vaccine: a view from over 20 years, The Lancet 366:1894-1898.*

Walker, B. D, and D. R. Burton, 2008, Toward an AIDS vaccine, Science 320:760-764.*

Levine, A. J., 2008, Why do we not yet have a human immunodeficiency virus vaccine?, J. Virol. 82(24):11998-12000.*

Ma, Meihui., et al. "Molecular Determinants for Cellular Uptake of Tat Protein of Human Immunodeficiency Virus Type 1 in Brain Cells." Journal of Virology, vol. 71, No. 3, May 1997, pp. 2495-2499.

Hyun, Young-Lan., et al. "Enzymic methylation of arginal residues in—Gly-Arg-Gly- peptides." Biochem. J. (2000) 348, pp. 573-578.

* cited by examiner

*Primary Examiner*—Jeffrey S. Parkin
(74) *Attorney, Agent, or Firm*—McDermott Will & Emery LLP

(57) ABSTRACT

Non-denatured, recombinant human immunodeficiency virus (HIV) Tat that is free of bacterial RNA and endotoxin is employed in an anti-HIV vaccine. A process of producing the recombinant Tat protein includes steps for removing bacterial RNA from the recombinant Tat and for removing endotoxin from the recombinant Tat protein. A Tat-adsorbed nanoparticle formulation and method of making the same. A method of vaccinating against and/or treating HIV infection comprises administering to a subject in need of such vaccination or treatment an immune-response inducing effective amount of the recombinant Tat protein.

18 Claims, 10 Drawing Sheets

A

B

A

B

SEQUENCE LISTING

<160> NUMBER OF SEQ ID NOS: 3

<210> SEQ ID NO 1
<211> LENGTH: 72
<212> TYPE: PRT
<213> ORGANISM: HIV

<400> SEQUENCE: 1

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Arg Ala His Gln Asn Ser Gln Thr
    50                  55                  60

His Gln Ala Ser Leu Ser Lys Gln
65                  70

<210> SEQ ID NO 2
<211> LENGTH: 86
<212> TYPE: PRT
<213> ORGANISM: HIV

<400> SEQUENCE: 2

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

-continued

```
Arg Lys Lys Arg Arg Gln Arg Arg Ala His Gln Asn Ser Gln Thr
    50              55                  60

His Gln Ala Ser Leu Ser Lys Gln Pro Thr Ser Gln Pro Arg Gly Asp
65              70                  75                  80

Pro Thr Gly Pro Lys Glu
                85

<210> SEQ ID NO 3
<211> LENGTH: 86
<212> TYPE: PRT
<213> ORGANISM: HIV
<220> FEATURE:
<221> NAME/KEY: MUTATION
<222> LOCATION: (22)..(22)
<223> OTHER INFORMATION: Cys 22 SUBSTITUTED FOR Gly

<400> SEQUENCE: 3

Met Glu Pro Val Asp Pro Arg Leu Glu Pro Trp Lys His Pro Gly Ser
1               5                   10                  15

Gln Pro Lys Thr Ala Cys Thr Asn Gly Tyr Cys Lys Lys Cys Cys Phe
                20                  25                  30

His Cys Gln Val Cys Phe Ile Thr Lys Ala Leu Gly Ile Ser Tyr Gly
            35                  40                  45

Arg Lys Lys Arg Arg Gln Arg Arg Ala His Gln Asn Ser Gln Thr
    50              55                  60

His Gln Ala Ser Leu Ser Lys Gln Pro Thr Ser Gln Pro Arg Gly Asp
65              70                  75                  80

Pro Thr Gly Pro Lys Glu
                85
```

COMPOSITIONS COMPRISING HUMAN IMMUNODEFICIENCY VIRUS TAT ADSORBED TO THE SURFACE OF ANIONIC NANOPARTICLES

RELATED APPLICATIONS

This application is a U.S. National Phase under 35 U.S.C. 371 of PCT.US03/05806 filed Feb. 27, 2003, which in turn claims the benefit of U.S. Provisional application No. 60/361,043, filed on Mar. 1, 2002 the entire contents of each of which are hereby incorporated by reference.

FIELD OF THE INVENTION

The present invention relates to therapeutic agents and methods for treating HIV infection. More specifically, the invention relates to compositions of matter that include an immunostimulatory recombinant transcriptional Tat protein of the HIV and a Tat-adsorbed nanoparticle that evoke T-helper (Th), cytotoxic T-lymphocyte (CTL), and antibody immune responses.

BACKGROUND OF THE INVENTION

The human immunodeficiency virus (HIV) is a member of the lentivirus family of animal retroviruses. Lentiviruses, including visna virus of sheep, and the bovine, feline and simian immunodeficiency viruses (SIV), are capable of long-term latent infection in cells and short-term cytopathic effects, and they all produce slowly progressive, fatal diseases, which include wasting syndromes and central nervous system degeneration. Two closely related types of HIV, designated HIV-1 and HIV-2, have been identified. HIV-1 and HIV-2 differ in genomic structure and antigenicity, sharing only 40 percent nucleic acid sequence homology. Nonetheless, both forms of HIV cause similar clinical syndromes.

HIV infection ultimately results in impaired function of both the specific and innate immune systems. The most prominent defects are in cell-mediated immunity and they can be attributed to a lack of CD4+ T cells, and/or abnormalities in immune system function with normal CD4+ T cell counts. The hallmark of the progression of HIV-induced disease is the diminishing number of CD4+ T cells in the peripheral blood, from a normal of about $1000/mm^3$ to less than $100/mm^3$ in fully developed AIDS. Since CD4+ helper T cells are essential for both cell-mediated and humoral immune responses to various microbes, the loss of these lymphocytes is a major reason why AIDS patients become susceptible to so many infections. The loss of CD4+ cells may occur after several months or take longer than 10 years in different individuals.

HIV gene expression may be divided into an early stage, during which regulatory genes are expressed, and a late stage, during which structural genes are expressed and full-length viral genomes are packaged. Expression of the early regulatory genes, including Tat, requires sequential RNA splicing events in the nucleus that generate short mRNAs, which are then transported to the cytoplasm and are subsequently translated into proteins. The Tat gene encodes a protein that binds to a sequence present in the long terminal repeats (LTR) called the transactivating response element (TAR), resulting in enhanced viral gene expression. Binding of the Tat protein to the viral LTR causes a 1000-fold increase in RNA polymerase II-catalyzed transcription of the provirus, and is required for replication of the virus (Abbas, A. K. et al. 1997 in Cellular and Molecular Immunology, ch 21, 450-459).

Tat is released from cells at relatively high levels and can be detected in the serum of HIV infected individuals. It is rapidly taken up by other cells through binding mediated by the basic domain of the molecule (Ma, M. and Nath, A. 1997 J. Virol. 71:2495). This feature allows extracellular Tat to transactivate latent HIV in other cells (Frankel, A. D. and Pabo C. O., 1998 Cell 55:1189; Li, C. J. et al. 1997 Proc. Natl. Acad. Sci. USA 94:8116). It also allows for Tat to transactivate other cellular processes, causing altered intracellular signaling in a variety of cell types (Li, C. J. et al. 1997 Proc. Natl. Acad. Sci. USA 94:8116; Viscidi, R. P. et al. 1989 Science 246:1606; Li, C. J. et al. 1995 Science 268:429; Westendorp, M. O. et al. 1995 Nature 375:497; Kolesnitchenko, V. et al. 1997 J. Virol. 71:9753). A consequence of these events is severe immunosuppressive. However, most of these studies have been conducted in vitro at nanomolar concentrations of Tat, and it is unclear to what extent this occurs in vivo. Extracellular Tat also causes rapid calcium fluxes in neurons and other cell types (Nath, A. et al. 1996 J. Virol. 70:1475; Nath, A. et al. 1996 J. Neurovirol. 2:17; Holden, C. P. et al. 1999 Neuroscience 91:1369; Haughney, N. J. et al. 1998 J. Neurovirol. 4:353; Nath, A. et al. 2000 Ann. Neurol. 47 (January 2000); Haughney, N. J. et al. 1999 J. Neurochem. 73:1363).

Interestingly, this rapid internalization of Tat also results in the efficient entry of Tat into the MHC class I processing pathway (Moy, P. et al. 1996 Mol. Biotechnol. 6:105; Fawell, S. et al. 1994 Proc. Natl. Acad. Sci. USA 91:664; Kim, D. T. et al. 1997 J. Immunol. 159:1666). In fact, a single peptide consisting of amino acids 49 to 57 of Tat was shown to facilitate the transport of ovalbumin (OVA) into the class I pathway (Moy, P. et al. 1996 Mol. Biotechnol. 6:105). Thus, the internalization of Tat and entry into the class I pathway would be expected to enhance the development of cytotoxic T-lymphocyte (CTL) responses aimed at Tat epitopes, if its transactivating activity were blocked. Inactivation of the transactivation responses aimed at Tat epitopes has been achieved by mutating residue Cys 22 to Gly. The mutated Tat functions as a dominant negative (Rossi, C. et al. 1997 Gene Ther. 4:1261; Caputo, A. et al. 1996 Gene. Ther. 3:235).

Several studies have shown that Tat is immunosuppressive. Tat can induce apoptosis in T cells by a process that involves activation of cellular cyclin dependent kinases (Li, C. J. et al. 1995 Science 268:429). Recently, Tat has been shown to up-regulate FasL on macrophages (Wu, M. X. and Schlossman, S. F. 1997 Pro. Natl. Acad. Sci. USA 94:13832; Dockrell, D. H. et al. 1998 J. Clin. Invest. 101:2394) and T cells (Westendorp, M. O. et al. 1995 Nature 375:497), resulting in apoptosis of the Fas expressing T cells. On the other hand, Tat has been shown to prevent apoptosis in some systems (Zauli, G. et al. 1993 Cancer Res. 53:4481). However, most of these studies have been conducted in vitro, and it is unclear to what extent Tat is immunosuppressive in vivo. A recent study by Cohen et al. (Cohen, S. S. et al. 1999 Proc. Natl. Acad. Sci. USA 96:10842) has shown that immunization using Tat in complete Freund's adjuvant (CFA) suppressed the response to a co-administered antigen, and that this effect was abrogated by oxidation of the Tat molecule. It would be desirable to evaluate the immunosuppressive properties of Tat in an in vivo system.

Tat from the human immunodeficiency virus type 1 (HIV-1) is an RNA binding transcriptional protein that is expressed early in HIV infection, and is necessary for high level expression of viral proteins (Garber, M. E. and Jones, K. A. 1999 Curr. Opin. Immunol. 11:460). Tat comprises 86 to 102 amino acids that are encoded by 2 exons, and Tat protein comprise five functional domains (Bayer, P. et al. 1995 J. Mol. Biol. 247:529). The first 72 amino acids are encoded by exon 1 and exhibit full transactivating activity. The amino terminal domain spans the first 21 amino acids; the cysteine-rich domain spans amino acids 22-37 and represents the transactivation domain; the basic domain spans amino acids 49-72, and contains the nuclear localization signal sequences, which facilitate the binding of Tat to Tat-responsive elements as well as the uptake of Tat by the cell (Jones, K. A. and Peterlin, B. M. 1994 Ann. Rev. Biochem. 63:717; Chang H. C. et al. 1997 Aids 11:1421; Barillari, G. et al. 1993 Proc. Natl. Acad. Sci. USA 90:7941). The second exon encodes the amino acid C-terminal sequence, which varies among different strains of HIV-1 from amino acids 73 to 86 or 73 to 102. The C terminus is not required for transactivation but does contain an RGD (arginine-glycine-aspartate) motif, which is important in binding to cell surface molecules and the extracellular matrix (Chang H. C. et al. 1997 AIDS 11:1421). The inventors have shown that the second exon of Tat influences the tertiary configuration of Tat and greatly potentiates Tat uptake (Ma, M. and Nath, A. 1997 J. Virol. 71:2495).

Tat is an unusual transcription factor as it can be released from cells and enter cells, while retaining its transactivating activity, which enables it to up-regulate a number of genes. It appears that the basic domain of Tat is important, not only for translocation and for nuclear localization but also for transactivation of cellular genes. As such, targeting of Tat protein or, more simply, the basic protein provides great scope for therapeutic intervention in HIV-1 infection.

Modern vaccines typically consist of either a killed (inactivated) or a live, nonvirulent (attenuated) form of an infectious agent. Traditionally, the infectious agent is grown in culture, purified, and either inactivated or attenuated without losing the ability to evoke an immune response that is effective against the virulent form of the infectious organism. Notwithstanding the considerable success that has been achieved in creating effective vaccines against numerous diseases, AIDS is one disease that is not preventable through the use of traditional vaccines.

The task of developing an effective vaccine for immunoprophylaxis against HIV has been complicated by the genetic potential of the virus for great antigenic variability. This effort has largely been directed to proteins of the virus that are expressed on the surface of infected cells, which are recognized by cytotoxic T cells. The T cell response eliminates infected cells, while free virus is blocked and cleared by antibodies to surface antigens of the viron. Limitations of this mode of vaccination are readily apparent in HIV-1, which has demonstrated a great diversity in immunogenic viral epitopes and rapid mutational variations that occur within and between infected individuals.

On the other hand, intracellular Tat is efficiently processed by major histocompatibility complex (MHC) class 1 for presentation to cytotoxic T lymphocytes (CTL). CTL responses have been detected repeatedly in individuals infected with HIV (van Baalen, C. A. et al. 1997 J. Gen. Virol. 78:1913; Venet, A. et al. 1992 J. Immunol. 148:2899; Froebel, K. S. et al. 1994 AIDS Res. Hum. Retroviruses 10:S83; Ogg, G. S. et al. 1998 Science 279:2103), and other studies have shown that the presence of anti-Tat CTL during the initial phase of infection, correlates inversely with the progression of the infection to AIDS disease (Re, M. C et al. 1995 J. Aquir. Immune Defic. Syndr. Hum. Retrovirol. 10:408). Tat also shows very little variation between HIV subtypes, and the first exon is highly conserved among the different subtypes, except the O subtype (Gringeri, A. et al. 1998 J. Hum. Virol. 1:293). Because of these properties, Tat is an attractive candidate as a vaccine. Current studies on the development of a Tat vaccine utilize inactivated Tat "toxoid" in an effort to prevent the toxic and immunosuppressive effects of Tat (Gringeri, A. et al. 1998 J. Hum. Virol. 1:293; Gallo, R. C. 1999 Proc. Nat. Acad. Sci. USA 96:8324; Gringeri, A. et al. 1999 J. Aquir. Immune Defic. Syndr. Hum. Retrovirol. 20:371). Tat toxoid has been administered in incomplete Freund's adjuvant to HIV seronegative people, and has been shown to safely induce modest antibody and DTH responses (Gringeri, A. et al. 1998 J. Hum. Virol. 1:293; Gringeri, A. et al. 1999 J. Aquir. Immune Defic. Syndr. Hum. Retrovirol. 20:371). However, the use of a denatured molecule may destroy important epitopes and prevent Tat from efficiently entering cells for an optimum immune response. Also, current immunization strategies would not be expected to induce T helper 1 (Th1), or CTL responses, which are critical for antiviral immune responses. Biologically active Tat has been used to immunize monkeys (Cafaro, A. et al. 1999 Nat. Med. 5:643). This vaccination protocol achieved partial protection against the highly pathogenic SHIV virus. However, it is conceivable that had the immunosuppressive effect of Tat been abolished, a better immune response could have been attained.

The present inventors have discovered that Tat produced by recombinant methods tightly binds bacterial RNA, which conventional methods of purification of recombinant Tat are unable to remove from the protein. This tightly bound RNA tends to mask antigenic sites (epitopes) on the Tat protein. Stimulation of the immune system by recombinant Tat protein is thereby attenuated, which in turn reduces the Tat protein's usefulness as a vaccine.

The present inventors have also discovered that highly purified Tat does not cause immuno-suppression when given as a vaccine in mice, while still inducing a strong immune response. Moreover, recombinant Tat has heretofore been purified by reverse-phase HPLC, which gives rise to denaturation of the protein and concomitant loss of important epitopes. Thus, the conventional purification methodology results in less-than-optimal immunogenic recombinant Tat protein.

Heretofore, Tat has been produced by synthetic procedures. While the primary structure (amino acid sequence) of Tat can be attained by such methodology, the harsh chemical conditions required for such synthesis tend to interfere with protein folding. Thus, it has not been heretofore possible to faithfully produce a Tat protein by synthetic methods that possess naturally occurring Tat protein's tertiary structure. As a result, purely synthetic methods tend to produce Tat protein that lacks some or all of the epitopes that are present in naturally-occurring Tat protein, again resulting in less-than-optimal immune stimulation by recombinant Tat protein.

There is thus a need for a method for producing a recombinant Tat protein that possesses a tertiary structure that has not been compromised by harsh synthetic chemicals.

There is also a need for a method for producing recombinant Tat protein that is free of masking of antigenic sites by bacterial RNA.

There is also a need for a recombinant Tat protein that possesses the ability to be internalized by cells and that is not immunosuppressive.

There is also a need for a recombinant Tat protein that is processed via the MHC class I pathway.

There is also a need for an effective immunogen and a method for effectively eliminating Tat-expressing cells by evoking strong Th1 and CTL responses, and resulting in an effective vaccine against HIV.

Furthermore, protein-based vaccines, such as recombinant Tat, are often more effective if administered with at least one adjuvant to enhance their potency (T. W. Baba, V. Liska, A. H.

khimani, N. B. Ray, P. J. Dailey, D. Penninck et al., Nat. Med. 1999 5 194-203). Unfortunately, after decades of research, insoluble aluminum salts. (generally called as "Alum") still represent the only approved adjuvants for human use in the US (R. K. Gupta, G. R. Siber, 1995 13 1263-1276). Alum has been used as vaccine adjuvant for many years. However, it is not a potent adjuvant for recombinant proteins, and more importantly, it does not help in cell-mediated immune responses (R. K. Gupta, E. H. Relyveld, E. B. Lindblad, B. Bizzini, S. Ben-Efraim, C. K. Gupta, Vaccine. 1993 11 293-306). It is well known that, with protein-based vaccines, Alum as adjuvant only helps humoral immune responses, characterized by enhanced antibody production and the type-2 CD4 T helper cell (Th2) responses, such as enhanced release of cytokines like interleukin 4 (IL-4) and/or the enhanced production of IgG subtype IgG1 (R. K. Gupta, G. R. Rost, E. Relyveld, G. R. Siber, Adjuvant properties of aluminum and calcium compounds, In: M. F. Powell, M. J. Newman (Eds.), Vaccine design: the subunit and adjuvant approach, Plenum Press, New York, 1995, p 229-248). Therefore, there exists a clear need to develop alternative and improved vaccine adjuvants and/or delivery systems, especially those that can help in cell-mediated immune responses, for protein-based vaccines, such as recombinant Tat protein.

Over the last several decades, many other potential vaccine adjuvants have been developed (M. Singh, D. T. O'Hagan, Nat. Biotech. 1999 17 1075-1081). Some of them were proven to help in cell-mediated immune responses. Lipid A is one example. The adjuvant effect of the lipopolysaccharide (LPS) from *Salmonella Minnesota* R595 (Re) was first described as early as in 1956 (J. T. Ulrich, K. R. Myers. Monophosphoryl lipid A as an adjuvant: past experiences and new directions. In: Vaccine design: The subunit and adjuvant approach, Ed (M. F. Powell, M. J. Newman) Plenum Press, New York, N.Y. 1995 p 495-524). The lipid A region of the LPS was found to be responsible for the adjuvanticity. Lipid A, which generally aids in Th1-type responses, enhances immune responses primarily through its ability to activate antigen-presenting cells (APC) and to induce the release of cytokines such as interferon-gamma (IFN-γ) and IL-2. The strong toxicity of lipid A promoted the development of the detoxified MPL, which retains the adjuvant properties of lipid A but with much reduced side effects (A. J. Johnson, Adjuvant action of bacterial endotoxins on the primary antibody response. In: M. Landy, W. Braun, (Eds.) Bacterial endotoxins. New Brunswick: University Press, 1964 pp 252-262; J. R. Baldridge, R. T. Crane, Monophosphoryl lipid A (MPL) formulations for the next generation of vaccines, Methods 1999 19 103-107). Besides the immunostimulatory molecules such as the lipid A, particulates as vaccine adjuvants have been evaluated for many years (D. T. O'Hagan, M. Singh, R. K. Gupta, Adv. Drug. Del. Rev. 1998 32 225-246). Particulates, such as emulsions, microparticles, ISCOMs, liposomes, virosomes, and the virus-like particles (VLP), have comparable dimensions to the pathogens the immune system evolved to combat. Therefore, it is reasonable to use particulates as a vaccine delivery system. One of the most extensively investigated is the poly (lactide-co-glycolide) (PLGA) microparticle. It has proven to be a potential vaccine adjuvant and/or delivery system for years (D. T. O'Hagan, J. Pharm. Pharmcol. 1998 59 1-10). Usually, vaccines were incorporated into the microparticles for delivery (O'Hagan, 1998). However, vaccines can also be adsorbed on the microparticles (J. Kreuter, P. P. Speiser, Infect. Immun. 1976, 13: 204-210). For example, Kazzaz et al. (2000) recently demonstrated that PLGA microparticles with adsorbed HIV-1 p55 gag protein on their surface were capable of inducing potent cell-mediated immune responses, including CTL, in mice following intramuscular immunization (J. Kazzaz, J. Neidleman, M. Singh, G. Ott, D. O'Hagan, J. Control. Rel. 2000 67 347-356). Surface adsorption of vaccines on microparticles has advantage in that it avoids the damages to vaccines caused by the sonication and high-torque mechanical mixing often needed in the process of microparticle preparation. In addition, limitation caused by the slowness of vaccine release once being incorporated can also be avoided. Singh et al. (M. Singh, M. Briones, G. Ott, D. O'Hagan, Proc. Natl. Acad. Sci. 2000 97 811-816) reported that the size of PLGA microparticles with adsorbed pDNA directly related to the strength of the resulting immune response; wherein the relative ratio was 300 nm>1 micron>30 microns. The authors attributed this particle size relationship to the enhanced ability of the smaller particles to be taken up by antigen presenting cells. Nevertheless, particles less than 300 nm were not investigated by the authors most likely since 300 nm particles that could be produced using the process described by the authors.

As such, there is a need for a method to engineer nanoparticles less than 300 nm and even less than 100 nm using a rapid and reproducible one-step process that may be contained in one vessel wherein said nanoparticles can be used to more efficiently target protein antigen to antigen presenting cells. There is also a need for an effective adjuvant and/or delivery system for Tat to enhance both humoral and cellular Th1-type immune responses.

SUMMARY OF THE INVENTION

The foregoing and other needs are met by embodiments according to the present invention, which provide a method of producing non-denatured, recombinant Tat protein that is free of bacterial RNA, the method comprising a step for removing bacterial RNA from the Tat protein and a method for purifying, without denaturing, Tat protein.

The foregoing and other needs are met by embodiments according to the present invention, which provide a non-denatured, recombinant Tat protein that is free of bacterial RNA.

The foregoing and other needs are further met by embodiments according to the present invention, which provide a method for inducing humoral and cellular responses that will lead to the destruction of HIV-infected cells, the method comprising administering to a subject, including a human subject, a humoral and cellular response inducing amount of a recombinant Tat protein with or without an adjuvant and/or Tat-delivery system according to the present invention.

BRIEF DESCRIPTION OF THE DRAWINGS

The present invention will become more fully understood from the detailed description given below. The accompanying drawings are presented for the purposes of illustration only, and thus are not intended to limit the scope of the present invention.

DETAILED DESCRIPTION OF THE INVENTION

In one aspect of the present invention there is a therapeutic agent for treating or preventing HIV infection. In some embodiments according to the present invention, a vaccine is provided that is capable of eliminating part or all HIV viral load from an infected host by targeting the immune system to HIV-infected cells. In some embodiments, the invention is directed to treating HIV-1 infection.

In some embodiments of the invention, the therapeutic agent includes an immunostimulatory recombinant Tat protein that retains the ability of being internalized by cells and acts as an effective immunogen for the development of Th1 and CTL responses. In some embodiments according to the present invention, the inventive Tat protein is administered to a patient in need of such treatment early in the course of infection, such as during the presymptomatic stage, alone or in combination with other subunit vaccines. In other embodiments, the inventive Tat protein is administered after the patient has manifested symptoms of HIV infection.

In another aspect of the present invention there is a method for treating HIV infection. The inventive method comprises administering a recombinant Tat protein that elicits humoral and cellular immune responses, while avoiding immune suppression. The humoral response provides neutralizing antibodies specific for Tat, which eliminates viral Tat protein that is released from HIV-infected cells. The cellular immune response induces the activation of Th1 and CTL cells, which then target and eliminate cells harboring HIV.

Figure 1:
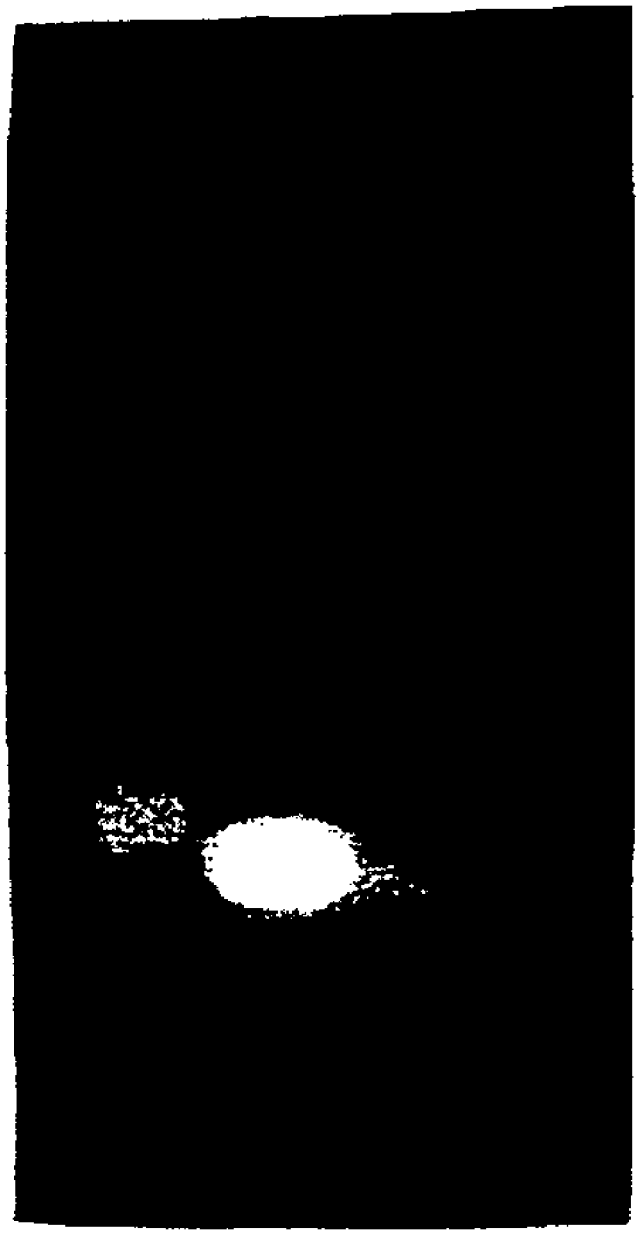
FIG. 1 shows Tat binding to RNA. Lane 1 shows molecular weight markers. Lane 2 shows transfer RNA. Lane 3 shows Tat protein (10 ug). Lane 4 shows Tat protein treated with highly purified RNase for 20 min at room temperature.

The present inventors have surprisingly discovered that recombinant Tat protein tightly binds bacterial RNA, which masks Tat epitopes. FIG. 1 shows Tat binding to RNA in samples analyzed by agarose gel electrophoresis followed by staining with ethidium bromide. The absence of signal in lane 4 suggests that the Tat protein binds to RNA which has the molecular mass of transfer RNA (1200 bp). The present inventors have further discovered that Tat protein copurifies with endotoxin, which may mask Tat epitopes, and/or suppress immune function. In a preferred embodiment a recombinant Tat protein is prepared that does not have RNA tightly bound to it, and that is substantially free of endotoxin contamination.

The present inventors have surprisingly discovered that recombinant Tat protein tightly binds bacterial RNA, which masks Tat epitopes. FIG. 1 shows Tat binding to RNA in samples analyzed by agarose gel electrophoresis followed by staining with ethidium bromide. The absence of signal in lane 4 suggests that the Tat protein binds to RNA which has the molecular mass of transfer RNA (1200 bp). The present inventors have further discovered that Tat protein copurifies with endotoxin, which may mask Tat epitopes, and/or suppress immune function. In a preferred embodiment a recombinant Tat protein is prepared that does not have RNA tightly bound to it, and that is substantially free of endotoxin contamination.

The present inventors have discovered that wild-type Tat 1-72 (SEQ ID NO: 1) is capable of inducing significant and specific humoral and T cell mediated immune responses, and that Tat 1-72 is not immunosuppressive in vivo. The term "wild-type" refers to an amino acid sequence encoded by a cDNA that is identical to that encoded by the endogenous gene. Tat refers to the protein product of the tat gene. In still another aspect of the present invention there is a recombinant Tat 1-72 (SEQ ID NO: 1) that faithfully reproduces both the primary and tertiary structure of naturally occurring, wild-type Tat 1-72 (SEQ ID NO: 1).

While the specific embodiments set forth below are directed to HIV-1, the purification and therapeutic methodologies set forth herein are equally applicable to HIV-2, owing to the recognized homology between the two viral strains. As used in the general discussion of the invention, "HIV" refers to HIV-1 or HIV-2, unless otherwise specified.

Preferably, some embodiments of the present invention provide methods for using a recombinant Tat protein for inducing humoral and cellular responses in an animal, preferably a mammalian animal, and more preferably a human. More preferably, the Tat protein is autonomously internalized by cells; that is, not integrated into the host genome. As mentioned above, the second exon of Tat influences the tertiary configuration of Tat and greatly potentiates Tat cellular uptake. Three forms of recombinant Tat proteins were evaluated for their immunogenic effects: Tat 1-86 (SEQ ID NO: 2), Tat 1-72 (SEQ ID NO: 1), and mutated Tat 1-86 (mTat1-86) (SEQ ID NO: 3). Tat 1-72 (SEQ ID NO: 1) protein was derived from the HIV-1 BRU exon 1; and Tat 1-86 (SEQ ID NO: 2) was derived from HIV-1 BRU exons 1 and 2. The HIV-1 BRU exons were obtained from Dr. Richard Gaynor through the AIDS repository at the NIH. Mutated Tat 1-86 (mTat 1-86) (SEQ ID NO: 3), which is derived from exon 1, was modified to contain a single amino acid substitution at position 22, whereby Cys 22 was substituted by a Gly using site directed mutagenisis (Rossi, C. et al. 1997 Gene Ther. 4:1261; Caselli, B. et al. 1999 J. Immunol. 162:5631). The protein mTat 1-86 is a transdominant Tat mutant that lacks HIV-1 transactivation activity, and has been shown to elicit immune response against wild-type Tat protein in a mouse model.

The method for preparing recombinant proteins has been described previously by the inventors (Ma, M. and Nath, A. 1997 J. Virol. 71:2495; Nath, A. et al. 1996 J. Virol. 70:1475; Nath, A. et al. 1996 J. Neurovirol. 2:17; Holden, C. P. et al. 1999 Neuroscience 91:1369; Haughey, N. J. et al. 1998 J. Neurovirol. 4:353; Nath, A. et al. 2000 Ann. Neurol. 47; Haughey, N. J. et al. 1999 J. Neurochem. 73:1363). Briefly, wild-type Tat 1-72 (SEQ ID NO: 1) and Tat 1-86 (SEQ ID NO: 2), and mTat 1-86 (SEQ ID NO: 3) were subcloned into a bacterial vector PinPoint Xa-2 (Promega) to express Tat as fusion proteins that are naturally biotinylated at the N-terminus. E. Coli bacteria were transformed with the resulting vector, and were grown in 200 ml of Luria Broth for 18 hours and in 2 L of Terrific Broth for 1 hour. The cells were harvested, and lysed, and the biotinylated Tat protein was purified by affinity chromatography using a soft release avidin resin. Tat was cleaved from the fusion protein by enzymatic cleavage using factor Xa, eluted and desalted using a PD 10 column. It is obvious to those skilled in the art that the genomic and amino acid sequence and length of Tat varies amongst different strains of HIV. Also, the protein could be produced in various strains of E. coli, other organisms or cells.

As mentioned above, the inventors have surprisingly discovered that bacterial RNA remains tightly associated with the Tat proteins throughout the purification process. In order to avoid masking of Tat epitopes by bound bacterial RNA, the recombinant Tat-bound RNA is removed by digestion with RNAse. Endotoxin was removed by adsorption onto polymixin B. The purified Tat was then stored as a 5% glycerol stock at −80° C. The protein preparation was analyzed by western blot and a LTR activation assay for purity, and for the presence of endotoxin. Typically, the method described yields 0.5 mg of protein per liter of bacterial culture. The protein is >98% pure, and contains less than 1 pg of endotoxin per gram of Tat protein. The purified Tat proteins were used in all processes of the present invention as described below.

In yet another aspect of the invention there is provided a therapeutic composition for treating HIV infection, said composition comprising an effective amount of an immunostimulatory recombinant Tat protein and an adjuvant. Suitable compositions according to the present invention comprise a physiologically acceptable or pharmacologically acceptable composition, suitable for use in a method of treating early HIV infection. Administering said protein evokes cellular and humoral responses that lead to the elimination of HIV-infected cells at early stages of infection, such as during the asymptomatic phase. While not wishing to be bound by theory, it is believed that this mode of action occurs by stimulating production of CTL, by stimulation of lytic cytokines by Th1 cells, by evoking antibody dependant cellular cytotoxicity or by complement-dependent cell lysis. In a preferred embodiment, the immunization protocol induces a Th1 and CTL response to effectively eliminate HIV infected cells that express viral Tat in vivo. In any case, administering the inventive recombinant Tat protein as an antigen to an animal or a patient infected with HIV, eliminates cells harboring the HIV and restores immune responses lost as a result of the infection. The method of administering may be oral, topical, nasal or parenteral. Parenteral administration may include intravenous, intramuscular, subcutaneous, intradermal or intraperitoneal. Most preferably, the therapeutic agent should be formulated so as to be suitable for parenteral administration to an animal, and to be suitable for treating humans.

Previously developed vaccines have combined the Tat antigen with either RIBI or Alum adjuvants, (Cafaro, A. et al. 1999 Nat. Med. 5:643), Tat-ovalbumin conjugates (Moy, P. et al. 1996 Mol. Biotechnol. 6:105), or Tat-encapsulated cationic liposomes (Huang, L. et al. 1995, Biochem. Biophys. Res. Commun. 217:761). Other vaccines have used plasmid DNA to express Tat protein in vivo. (Caselli, E. et al. 1999 J. Immunol. 162:5631). However, the CTL responses to these immunization strategies have been inadequate or remain uncharacterized. Alternatively, previous immunization protocols using particulate forms of antigen have induced strong T cell proliferative responses. The previously devised particulate delivery systems include polylactic acid-co-glycolic acid (PLGA) microspheres (Cleland, J. L. et al. 1998 J. Pharm. Sci. 87:1489; Partidos, C. D. et al. 1997 J. Immunol. Methods 206:14345-47; Israel, Z. R. et al. 1999 AIDS Res. Hum. Retroviruses 15:1121), liposomes (Eckstein, M. et al. 1997 Vaccine 15:220; Lutsiak, C. M. et al. 1998 J. Pharm. Sci. 87:1428; Zheng, L. et al. 1999 AIDS Res. Hum. Retroviruses 15:1011; Zhou, F. et al., 1992 J. Immunol., 149:1599), and alginate microspheres (Bowersock, T. L. et al., 1999, Vaccine 17:1803; Bowersock, T. L. et al., 1998, Immunol. Lett. 60:37; Cho, N. H. et al., 1998, J. Controlled Release 53:215). However, the disadvantages of the previously used particulate systems include that that they are difficult and expensive for large-scale production. Because the peptide antigen is encapsulated in the particulate delivery system during the manufacturing process, the stability of the peptide must withstand high-torque mechanical forces during the mixing step(s). Control of optimal particle size, encapsulation efficiency and separation of unencapsulated protein from the particulate carrier are also problematic.

The present inventors have devised a particulate system that includes hydroxypropyl cellulose (HPC), which forms gel-particles containing Tat spontaneously at 35-37° C., and avoids potentially damaging high-torque mechanical mixing needed to entrap the antigen.

Figure 2:
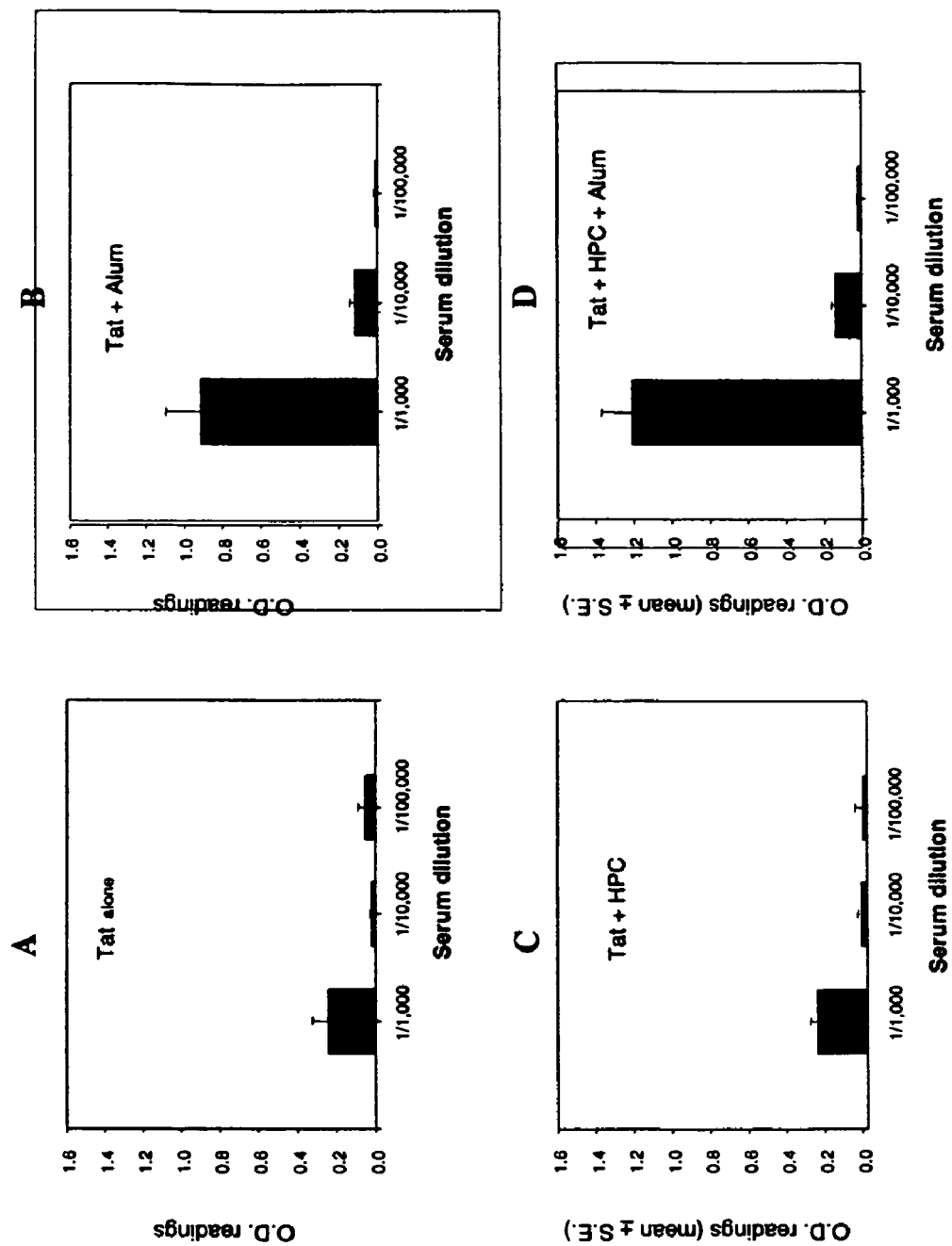
FIG. 2 shows a bar diagram that depicts the specific antibody response of four groups of mice that had been immunized with recombinant Tat 1-72 (SEQ ID NO:1) alone (a), and in combination with Alum (b), HPC (c), and HPC and Alum (d), according to the protocol described in Example 1 (a).

The present inventors have shown that administering an immunostimulatory recombinant Tat protein with an adjuvant to an animal induces significant and specific humoral and T cell responses. The present inventors assessed T cell and antibody responses in groups of mice that had been immunized subcutaneously with Tat 1-72 alone or in combination with one of the adjuvants: Alum (aluminum hydroxide), HPC, or ALUM+HPC. As shown in FIG. 2, significant antibody responses were attained, in all four groups with the greatest responses seen in the Tat+Alum and Tat+HPC+Alum groups. The latter groups achieved a total anti-Tat antibody titre of about 1:2000. Isotype specific ELISA revealed a predominant IgG1 antibody response, and no detectable IgG2 antibodies. This result indicates that Tat 1-72 elicits a substantial humoral response. The inventors envision that several types of particulate material including but not limited to the following: liposomes, nanoparticles and microspheres may be used to generate an immune response to Tat.

Figure 3:
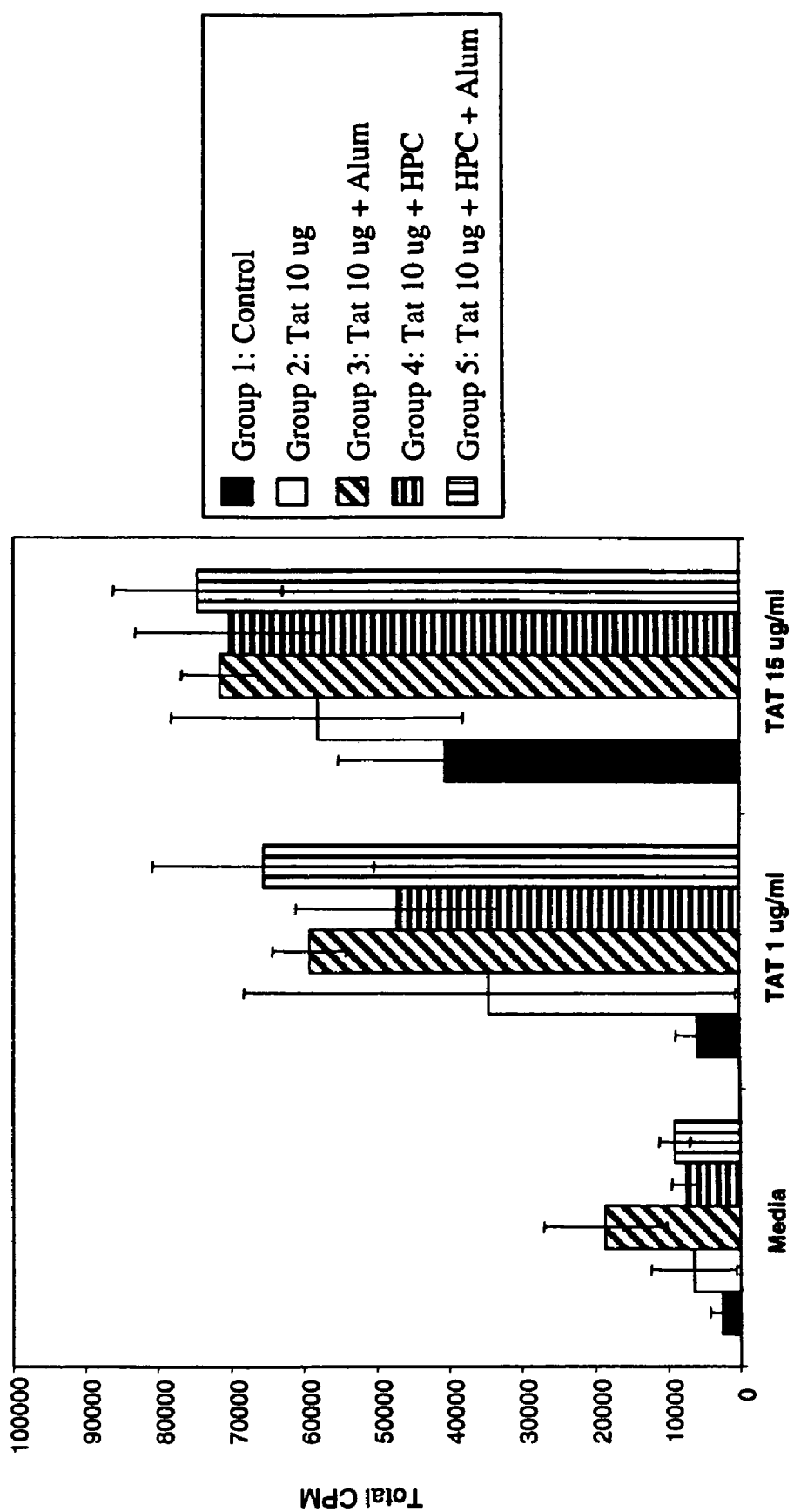
FIG. 3 shows a bar diagram that depicts the induction of Tat 1-72 (SEQ ID NO:1) specific T cell responses from mice that had been immunized with Tat 1-72 (SEQ ID NO:1). T cell proliferation was determined in the absence or the presence of Tat 1-72 (SEQ ID NO:1) at a concentration of 1 μg/ml or 10 μg/ml, according to the protocol described in Example 1 (b).

The auxiliary and inguinal lymph node cells of the mice immunized with Tat 1-72, were isolated and cultured for 5 days in the presence or absence of Tat 1-72, and T cell proliferation was determined by $^3$H-Tdr during the last 18 hours of the 5-day incubation. The inventors discovered that Tat 1-72 immunization induces Tat-specific T cell proliferation from the draining lymph nodes. (FIG. 3). The naive T cells from the control group proliferated significantly in response to 15 μg/ml (1 μM) Tat 1-72, which indicates that Tat 1-72 is mitogenic at this concentration. In contrast T cells from Tat 1-72-immunized mice showed even greater proliferation in the presence of 1 μg/ml concentration of Tat 1-72, indicating that the proliferative T cell response is specific to the Tat antigen. Therefore, recombinant Tat 1-72 is capable of inducing significant and specific humoral and T cell mediated responses.

The immune system of the mouse is very similar to the human immune system, and the person having skilled in the art will recognize that successful induction of anti-Tat immune response in the mouse model is strongly predictive of a similarly effective immune response in humans.

Figure 4:
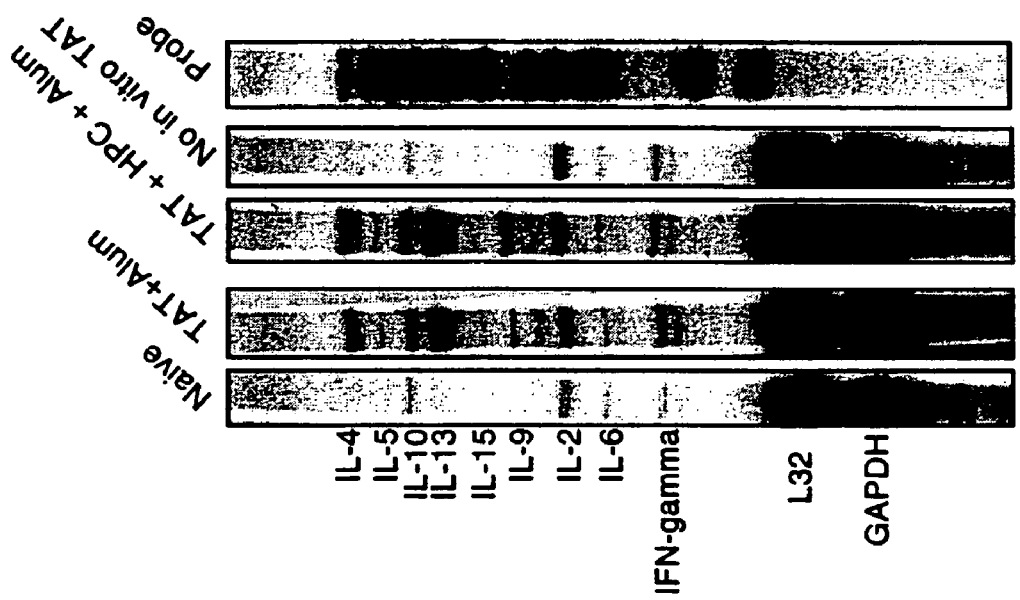
FIG. 4 shows the result of an RNAse protection assay that was performed according to the protocol outlined in Example 1 (c). The protected RNA fragments correspond to the cytokines that are expressed by Tat immune T cells in response to 1 μg/ml Tat 1-72 (SEQ ID NO:1).

To determine the cytokine profile of the Tat-specific T cells, cytokine mRNA levels were quantitated by multiprobe ribonuclease protection assay (Pharmingen) (FIG. 4). The cytokines expressed were predominantly IL-4, IL-9, IL-13 with relatively low levels of INF-γ, indicating a Th2 response. The production of IgG1 and Th2 T cell response are consistent with the known Th2 inducing property of Alum (Brewer, J. M. et al. 1999 J. Immunol. 163:6448).

Another embodiment of the present invention provides for a recombinant Tat protein that is not immunosuppressive. Several studies cited above have shown that Tat is immunosuppressive. However, the present inventors have discovered that neither Tat 1-72 nor Tat 1-86 produced by the foregoing process (i.e. RNAse digestion and polymixin column treatment) show any immunosuppressive effects. This result is surprising and unexpected. While not wishing to be bound by theory, it is believed that this result can be at least in part explained by differences between the previously developed experimental protocols and the protocol according to the present invention, and in particular the absence from the inventive TAT 1-72 and Tat 1-86 of bacterial RNA and cytotoxin, as well as the retention of the folding structure of the recombinant proteins.

The previous studies on the apoptotic effect of Tat were carried out in vitro, while the present inventors evaluated Tat-induced immunosuppression in vivo using the in vivo DO11.10 TCR transgenic T cell adoptive transfer system. In this system, T cells from mice that are sensitized to OVA are transferred to a normal BALB/c mouse, and clonal expansion of antigen specific T cells in response to OVA or OVA that is coinjected with a form of Tat, can be measured by flow cytometry using clonotypic monoclonal antibody KJ1-26 (Pape, K. et al. 1997 Immunol. Revl. 56:67). Following adoptive transfer of OVA specific D01 1.10 TCR transgenic cells into normal BALB/c mice, clonal expansion was observed by flow cytometry of lymph node (LN) or spleen cells in response to OVA immunization. This response is dependent on OVA presentation in a class II restricted manner on APCs and requires B7-CD28 interaction (Kearney, E. R. et al. 1995 J. Immunol. 155:1032). Because Tat 1-86 was shown to suppress the response to a coinjected antigen in another system (Cohen, S. S. et al. 1999 Proc. Natl. Acad. Sci. USA 96:10842), the inventors expected that Tat 1-86 would also suppress the response to OVA in their system. Surprisingly, when Tat 1-72 or Tat 1-86 were tested, neither protein caused immunosuppression of systemic clonal expansion displayed any immunosuppressive activity. A representative result is shown in Example 2 and the accompanying FIG. 5.

The present inventors have also devised a nanoparticle delivery system for delivering recombinant Tat protein. In still another embodiment, the present invention provides Tat-adsorbed nanoparticles. Tat-adsorbed nanoparticles are used to improve both antibody production and cell-mediated immune responses. It has also been shown that administering an immunostimulatory recombinant Tat protein with a nanoparticle-based vaccine delivery system to an animal induces enhanced humoral and Th1-type cellular immune response. The present inventors assessed antibody and T-cell responses in groups of mice that had been immunized subcutaneously with Tat 1-72 adjuvanted with Alum or lipid A, and Tat-adsorbed nanoparticles.

First, anionic nanoparticles were prepared as previously described in Cui, Z. and Mumper, R. J., Coating of Cationized Protein On Engineered Nanoparticles Results In Enhanced Immune Responses. Int J Pharm. 2002 238 (1-2):229-39, incorporated herein by reference in its entirety. Briefly, emulsifying wax (2 mg) was accurately weighed into 7-ml glass scintillation vials and melted on a hot plate at 50-55° C. Seven hundred (700) μL of de-ionized and filtered (0.22 μm) water were added to the melted wax while stirring to form homogenous milky slurry. Then, 300 μL of SDS stock solution (50 mM) were added while stirring to obtain a final SDS concentration of 15 mM. Within seconds, clear O/W microemulsions formed. These microemulsions were then simply cooled (cured) to room temperature while stirring to form nanoparticles. For particle sizing, the nanoparticle suspension was diluted with de-ionized and filtered (0.22 μm) water and the particle size was measured at 90° light scattering for 90 s at 25° C. The zeta potential of engineered nanoparticles was also measured using a Zeta Sizer 2000 from Malvern Instruments, Inc. (Southborough, Mass.).

The nanoparticles were purified using gel permeation chromatography (GPC) with a Sephadex G-75 column. Varying amounts of Tat in water were then added into the purified nanoparticle suspension followed by gently pipetting and slightly vortexing. The mixtures were then allowed to stay on laboratory bench for at least 30 min for binding before further use.

Figure 6:
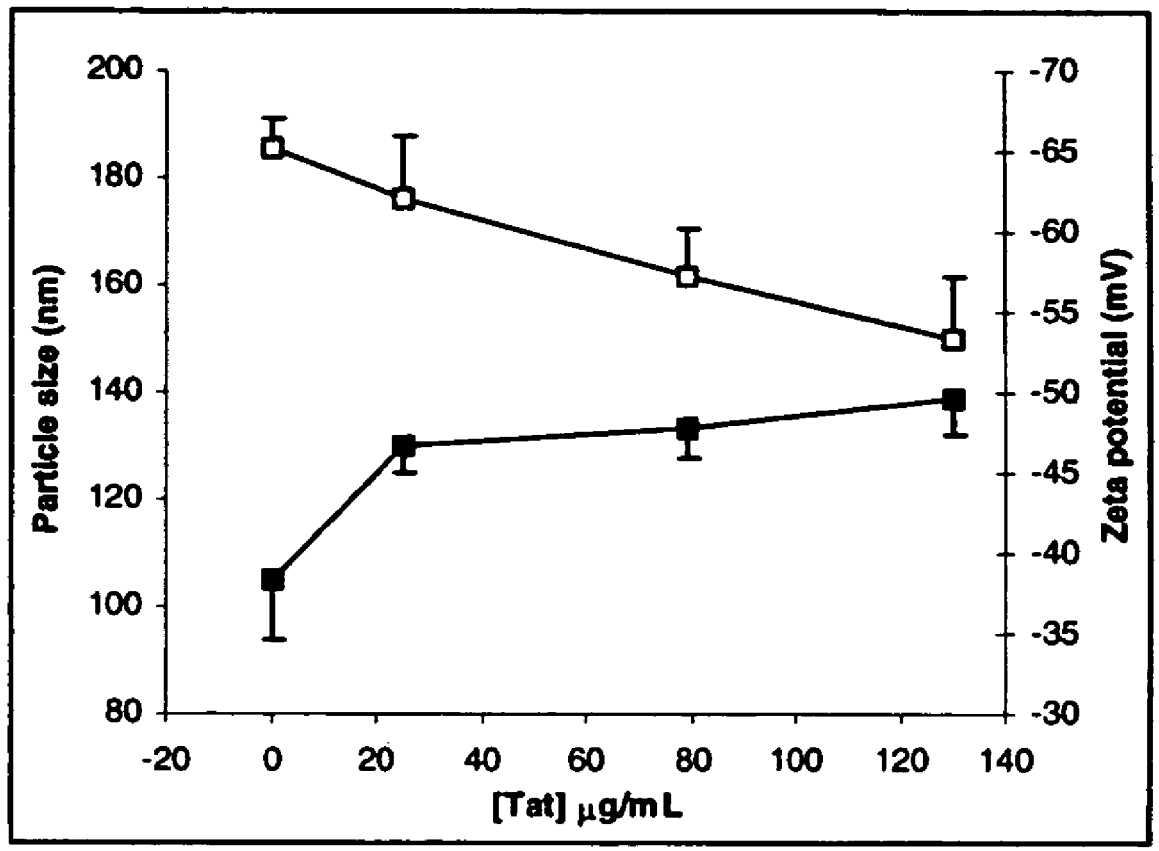
FIG. 6 shows the effect of the concentration of Tat on the particle size ( ) and zeta potential ( ) of the resulting Tat-adsorbed nanoparticles. Data reported were mean±S. D. (n=3).
Figure 7:
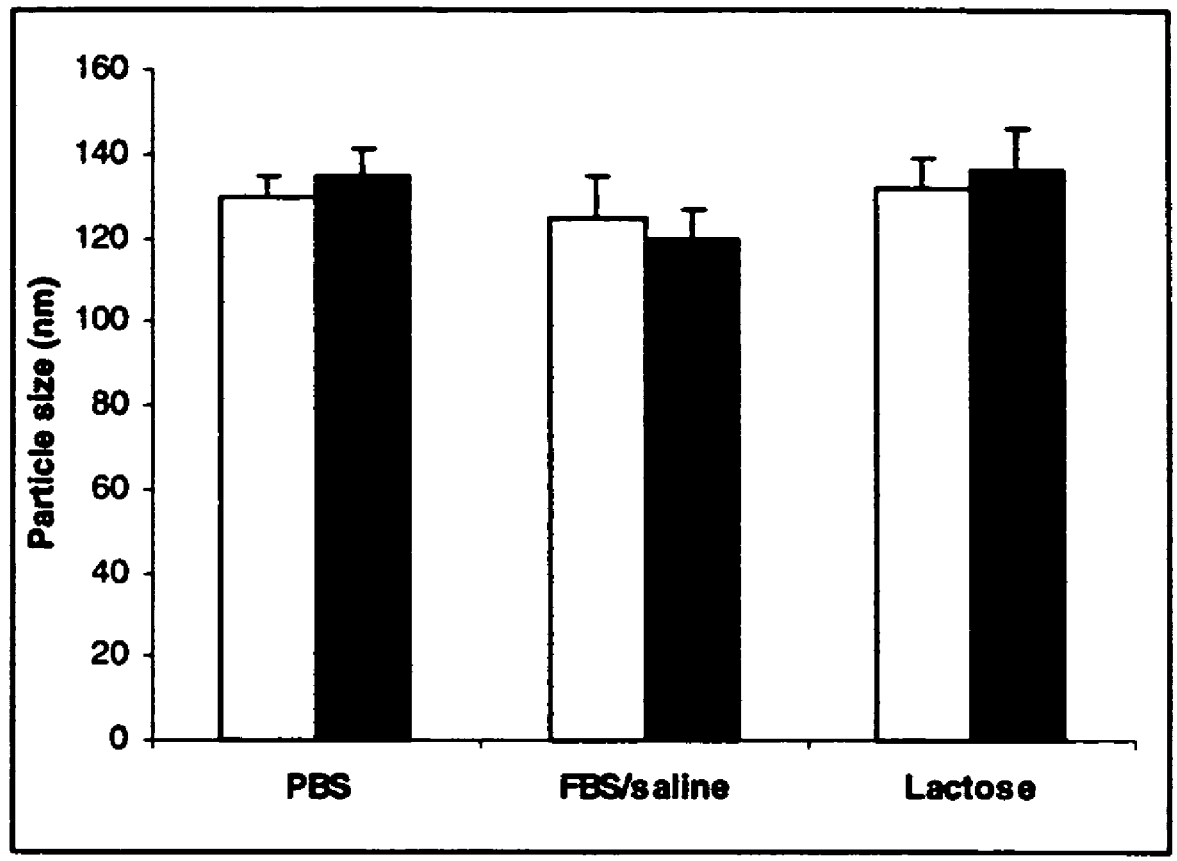
FIG. 7 shows the stability of the Tat-adsorbed nanoparticles in simulated biological media. The particle sizes were measured prior to incubation (white bars) and after incubation (black bars).

Then, the present inventors prepared Tat-adsorbed nanoparticles. As used herein, "Tat-adsorbed nanoparticles" refers to the adhesion of Tat protein to the surface of nanoparticles. HIV-1 Tat is a small protein encoded by two exons. The basic domain (aa 49-72) is rich in basic amino acids, which rendered the protein to be overall positively charged (K. A. Jones, B. M. Peterlin, Ann. Rev. Biochem. 1994 63 717). Therefore, Tat was able to bind on the surface of the anionic nanoparticles via strong electrostatic interactions. As shown in FIG. 6, the particle size and the zeta potential of the nanoparticles prior to protein binding were 105±11 nm and −65.1±2 mV, respectively. With more Tat being adsorbed on the surface of the nanoparticles, the size of the resulted nanoparticles increased, and the zeta potential of the nanoparticles became less negative. At a final Tat concentration of 25 μg/mL, the adsorption efficiency of Tat to the anionic nanoparticles was approximately 100% as confirmed by both gel permeation chromatography and ultrafiltration (MW cut-off, 50 kDa). This can be attributed to the fact that excess of anionic nanoparticles were used for adsorption. The Tat-adsorbed nanoparticles were stable in several simulated biological media as shown in FIG. 7. It was estimated that there were approximately 6-7 Tat molecules being adsorbed on each nanoparticle (final Tat concentration, 25 μg/mL).

Further, the present inventors have shown that Tat adsorbed nanoparticles result in enhanced humoral and Th-1 type immune response. Both humoral and Th-1 type cellular immune responses were assessed in groups of mice that had have been immunized subcutaneously with Tat 1-72 adjuvanted with Alum, Tat 1-72 adjuvanted with lipid A, and Tat-adsorbed nanoparticles. Ten to twelve week old female mice (Balb/C) from Harlan Sprague-Dawley Laboratories were used for all animal studies.

Three groups of mice were immunized with doses of either (i) Tat (5 μg)-coated nanoparticles (15-20 μg), (ii) 5 μg of Tat adjuvanted with 15 μg of Alum as a control for Th2 immune responses, or (iii) 5 μg of Tat adjuvanted with 50 μg of lipid A as a control for Th1 immune responses. In addition, 5 naïve mice were untreated and used as negative control. Two hundred (200) μl of each formulation in 10% lactose was injected on one site on the back. Prior to immunization, mice were anesthetized using pentobarbital (i.p.). On day 28, the mice were anesthetized and bled by cardiac puncture. Sera were separated and stored at −20° C. for assessment of antibody and T cell proliferative responses.

After immunization and according to previously described methods (Cui and Mumper, Int. J. Pharm. 2002 238 (1-2): 229-39), the present inventors compared using ELISA Tat-specific antibodies (IgG and IgM) in serum of Tat-adsorbed nanoparticles to Tat adjuvanted with Alum or lipid A. Briefly, Costar high binding 96-well assay plates were coated with 50 μL of Tat protein (8 μg/mL) overnight at 4° C. The plates were then blocked for 1 hr at 37° C. with 4% bovine serum albumin (BSA)/4% NGS (Sigma) solution (100 μL/well) made in 1×PBS/Tween 20 (Scytek). Mouse serum (50 μL/well, diluted for appropriate folds in 4% BSA/4% NGS/PBS/Tween 20) was incubated for 2 hr at 37° C. After washing three times with PBS/Tween 20 buffer, anti-mouse IgG HRP F(ab')$_2$ fragment from sheep or Goat Anti-Mouse IgM-HRP (Southern Biotechnology Associates, Inc., Birmingham, Ala.) (diluted 1:3,000 in 1% BSA) was added (50 p/well) and incubated for 1 hr at 37° C. Plates were washed three times with PBS/Tween 20 buffer. Finally, the samples were developed with 100 μL TMB substrate for 30 min at room temperature and then stopped with 50 μL of 0.2 M $H_2SO_4$. The optical density (OD) of each well was measured using a Universal Microplate Reader (Bio-Tek Instruments, Inc., Winooski, Vt.) at 450 nm.

As shown in FIGS. 8A and 8B, the antibody titers-from mice immunized with Tat-adsorbed nanoparticles, and Tat adjuvanted with Alum or lipid A were strong. The data showed Tat-adsorbed nanoparticles was comparable to that from the mice immunized with Tat adjuvanted with Alum.

To determine the cytokine release and the proliferation of isolated splenocytes of Tat-adsorbed nanoparticles in comparison to Tat adjuvanted with Alum and Tat adjuvanted with lipid A, splenocyte preparation was completed as previously described above (Cui and Mumper, Int J. Pharm. 2002 238 (1-2)229-39). Briefly, spleens from each group of mice were pooled together and placed into 5 mL of HBSS (Hank's Balanced Salt Solution) (1×) in a Stomacher Bag 400 from Fisher Scientific (Pittsburgh, Pa.). The spleens were homogenized at high speed for 60 s using a Stomacker Homogenizer. Cell suspensions were then transferred into 15 mL Falcon tube and filled to 15 mL with 1×ACK buffer (156 mM of $NH_4Cl$, 10 mM of $KHCO_3$, and 100 μM of EDTA) for red blood cell lysis. After 5-8 min at room temperature, the suspension was spun down at 1,500 rpm for 7 min at 4° C. After pouring off the supernatant, the cell pellet was re-suspended in 15 mL HBSS. The suspension was then spun down at 1,500 rpm for 7 min at 4° C. After washed once with 15 mL of RPMI-1640 (BioWhittaker, Walkersville, Md.) supplemented with 10% fetal bovine serum (FBS) (Sigma, St. Louis, Mo.) and 0.05 mg/mL of gentamycin (Gibco BRL), the cells were re-suspended in RPMI 1640 media (5 mL).

For cytokine release, isolated splenocytes ($1 \times 10^6$ cells/well) with three replicates (n=3) were seeded into a 48-well plate. (Costar), and stimulated with 2 μg/well of Tat protein. After incubation at 37° C. with 5% $CO_2$ for 48 hours, the splenocytes were spun down and the supernatant was collected and stored at −20° C. prior to further use. Cytokine concentration (IFN-γ and IL4) in the supernatants was determined using ELISA kits from Pierce-Endogen (Rockford, Ill.).

For splenocyte proliferation, isolated splenocytes ($1 \times 10^6$ cells/well) with three replicates (n=3) were seeded into a 48-well plate (Costar), and stimulated with 0 or 2 μg/well of Tat protein. After incubation at 37° C. with 5% $CO_2$ for 96 hours, 60 μL of the combined MTS/PMS solution (Promega) was pipetted into each well (20 μL/100 μL of cells in medium). After an additional 4.5 hours of incubation at 37° C. with 5% $CO_2$, the absorbance at 490 nm was measured using a Universal Microplate Reader. The cell proliferation was reported as the % increase of the $OD_{490}$ of the stimulated cells (2 μg/well) over the $OD_{490}$ of un-stimulated cells (0 μg/well) (i.e., $100 \times (OD490_{stimulated} - OD490_{un-stimulated}) / OD490_{un-stimulated}$).

Figure 9:
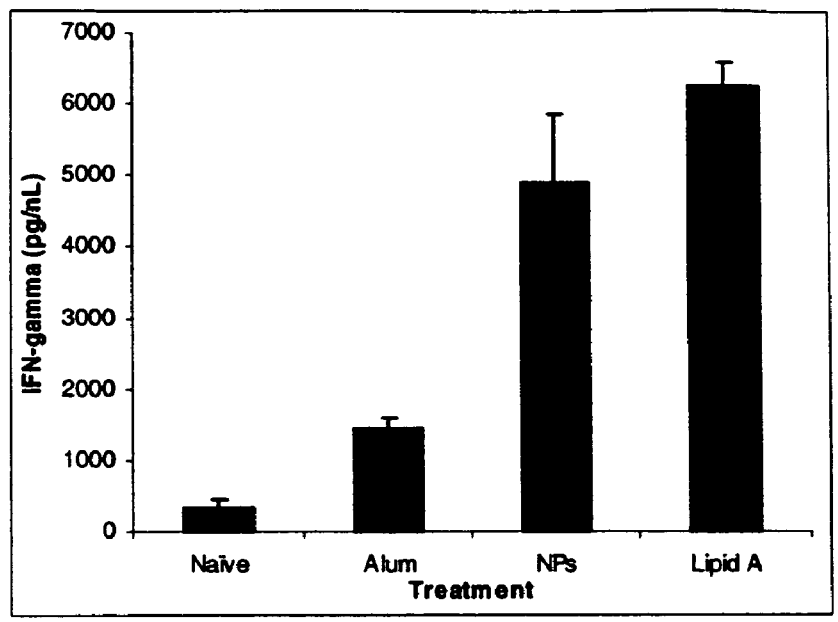
FIG. 9 shows release of cytokines from isolated splenocytes recovered from mice immunized with either Tat adjuvanted with Alum, Tat adsorbed on nanoparticles (NPs), or Tat adjuvanted with lipid A on day 0 and day 14. Data reported were mean±S. D. (n=3). * indicates the INF-γ releases from the NPs and lipid A groups were different from that of the others.  indicates the INF-γ release from the Alum group was greater than that from the naïve. * indicates that the IL-4 release from the NPs was significantly lower than that from the Alum.
Figure 9:
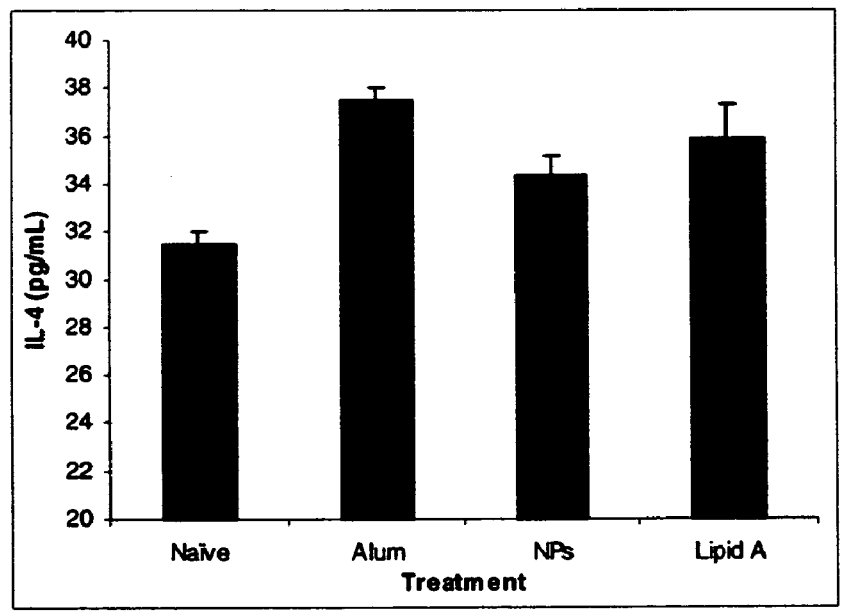
Figure 10:
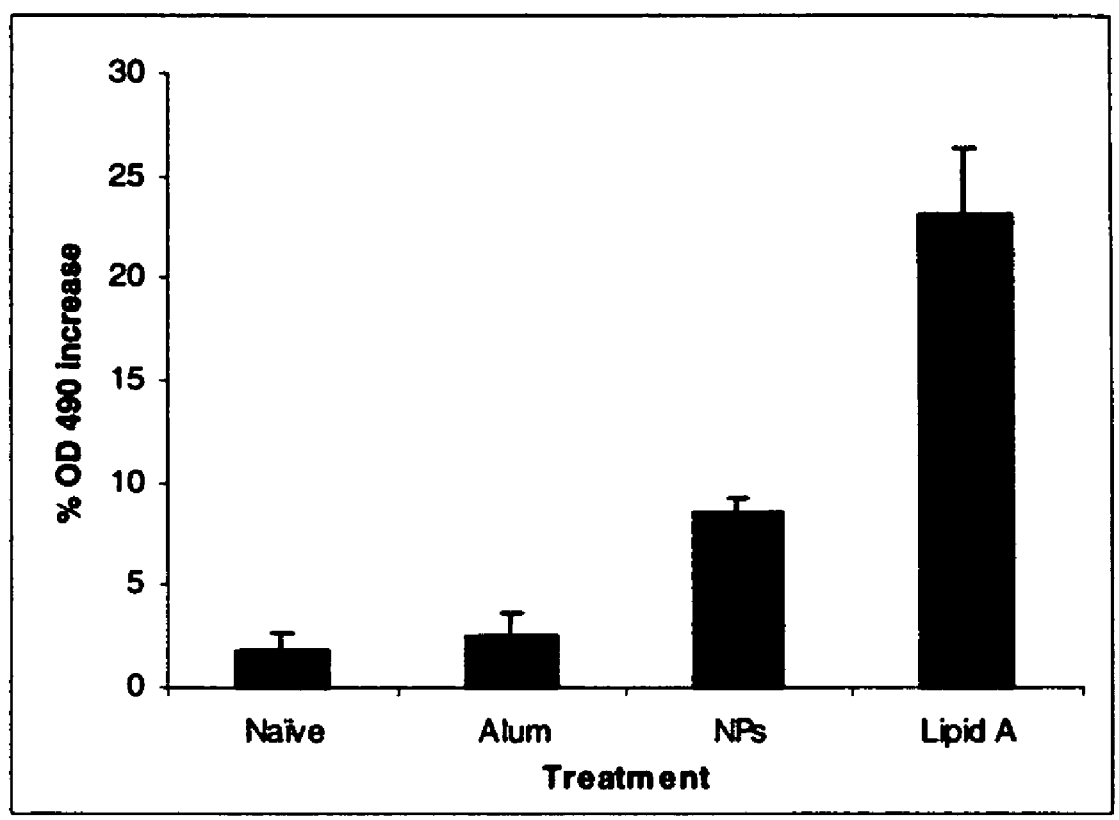
FIG. 10 illustrates in vitro proliferation of isolated splenocytes recovered from mice immunized with either Tat adjuvanted with Alum, Tat adsorbed on nanoparticles (NPs), or Tat adjuvanted with lipid A on day 0 and day 14. Data reported were mean±S. D. (n=3). * indicates that the result from the NPs group was significantly different from that of the others.

A representative result for Tat-adsorbed nanoparticle cytokine release and cell proliferation are shown in Example 4 and the accompanying FIGS. 9 and 10.

Another embodiment of the present invention provides a method for inhibiting HIV infection in an animal. Said method comprises administering a pharmacologically active amount of immunostimulatory recombinant Tat protein to an animal, preferably in a mammalian animal, and more preferably in a human.

In another aspect of the present invention, Tat-adsorbed nanoparticles provides a delivery system for, and a method for delivering, other protein antigens. The Tat-adsorbed nanoparticles delivery system is used in the treatment and prevention of cancer and infectious disease.

The present invention may be more fully appreciated upon consideration of the following, non-limiting, examples.

EXAMPLES

Example 1

Tat 1-72 Induces Humoral and Cell Mediated Responses

The present example is provided to demonstrate the effectiveness of Tat 1-72 as an immunogen.

(a) To determine the immunogenicity of Tat 1-72, 4 groups each of 5 mice were immunized with 10 μg of purified Tat alone, Tat+Alum, Tat+HPC, or Tat+HPC+Alum. The mice were immunized subcutaneously at one-week intervals for three weeks. At the end of the fourth week, serum was collected from each animal, and antibody and T cell proliferative responses were assessed. Tat specific antibodies were detected by sandwich ELISA on Tat coated ELISA plates, and using rabbit-anti-mouse Ig secondary antibody. The results are shown in FIGS. 2(A)-(D).

Significant Tat-specific antibody responses were obtained in all four groups. The strongest response was induced in the two animal groups which had been immunized with Tat in combination with Alum or HPC+Alum. The antibody titre for both groups was 1:2000. Isotype-specific ELISA revealed a predominant IgG1 response, and no detectable IgG2 antibodies.

(b) To determine the ability of Tat 1-72 to induce Tat-specific T cell proliferation. Four groups each of 5 mice were immunized as described above. A fifth group of mice was used as a control group, which was not immunized with Tat 1-72. The axilliary and inguinal lymph node cells were isolated, and cultured for 5 days in the presence or absence of either 1 ug/ml or 15 µg/ml Tat 1-72. Proliferation of the T cells was determined as a function of incorporation of $^3$H-Tdr during the last 18 hours of incubation.

The results are shown in FIG. 3. Tat 1-72 induced proliferation of naive T cells from the control group at the Tat 1-72 concentration of 15 µg/ml. I µg/ml Tat 1-72 did not have a significant effect on the proliferation of the naive T cells. However, Tat 1-72 induced significant increase in the proliferation of the T cells from the Tat-immunized animals. The significant changes were seen when either concentration of 1 µg/ml or 15 µg/ml Tat 1-72 was used. This result indicates that the proliferative response was Tat 1-72-specific.

(c) To determine the cytokine profile of the proliferating T cells, cytokine mRNA levels were quantitated as follows. Tat-immune T cells in culture were incubated with 1 µg/ml Tat 1-72 for three days. Total T cell RNA was isolated by guanidinium isothiocynate, and extracted using phenol. The RNA was hybridized to 32P-labelled RNA probes using the Pharmingen MCK-1 multiprobe cytokine ribonuclease protection kit. After hybridization, unprotected RNA was digested using RNAse, and the protected fragments were resolved on a 8% polyacrylamide/urea sequencing gel. The gel was dried, and the RNA bands were visualized and quantitated using a Storm 860 phosphor imager.

The results of the assay are shown in FIG. 4, and show that the cytokines that were predominantly expresses were IL-4, IL-9 and IL-13. Relatively low levels of INF-γ were also observed.

Example 2

Tat 1-72 does not Induce Immunosuppression In Vivo

The present example is provided to show the utility of Tat 1-72 as an immunogen, which does not induce immunosuppression.

The applicants used the in vivo D01 1. 10 TCR transgenic T cell adoptive transfer system to evaluate the effect of Tat 1-72 on the ability of D01 0. 11 T cells to undergo clonal expansion in vivo. OVA-specific DO 10.11 TCR transgenic T cells were transferred to normal BALB/c mice, and clonal expansion of the T cells was evaluated following administration of OVA in the presence or absence of Tat 1-72. D01 0.11 T cells, equivalent to 2.5×10 6 KJI 26, CD4+ cells, were transferred by intravenous administration into unirradiated BALB/c mice. Three days later, three groups of mice were given 200 µg OVA peptide 323-339, OVA 323-339 in combination with 10 µg Tat 1-72, or OVA 323-339 in combination with 10 µg Tat 1-86. The injections were repeated on two consecutive days. Axillary and inguinal lymph node cells were isolated on the third day. The cells were stained with KJI-26-FITC and anti-CD4-PE, and quantitated by flow cytometry.

Figure 5:
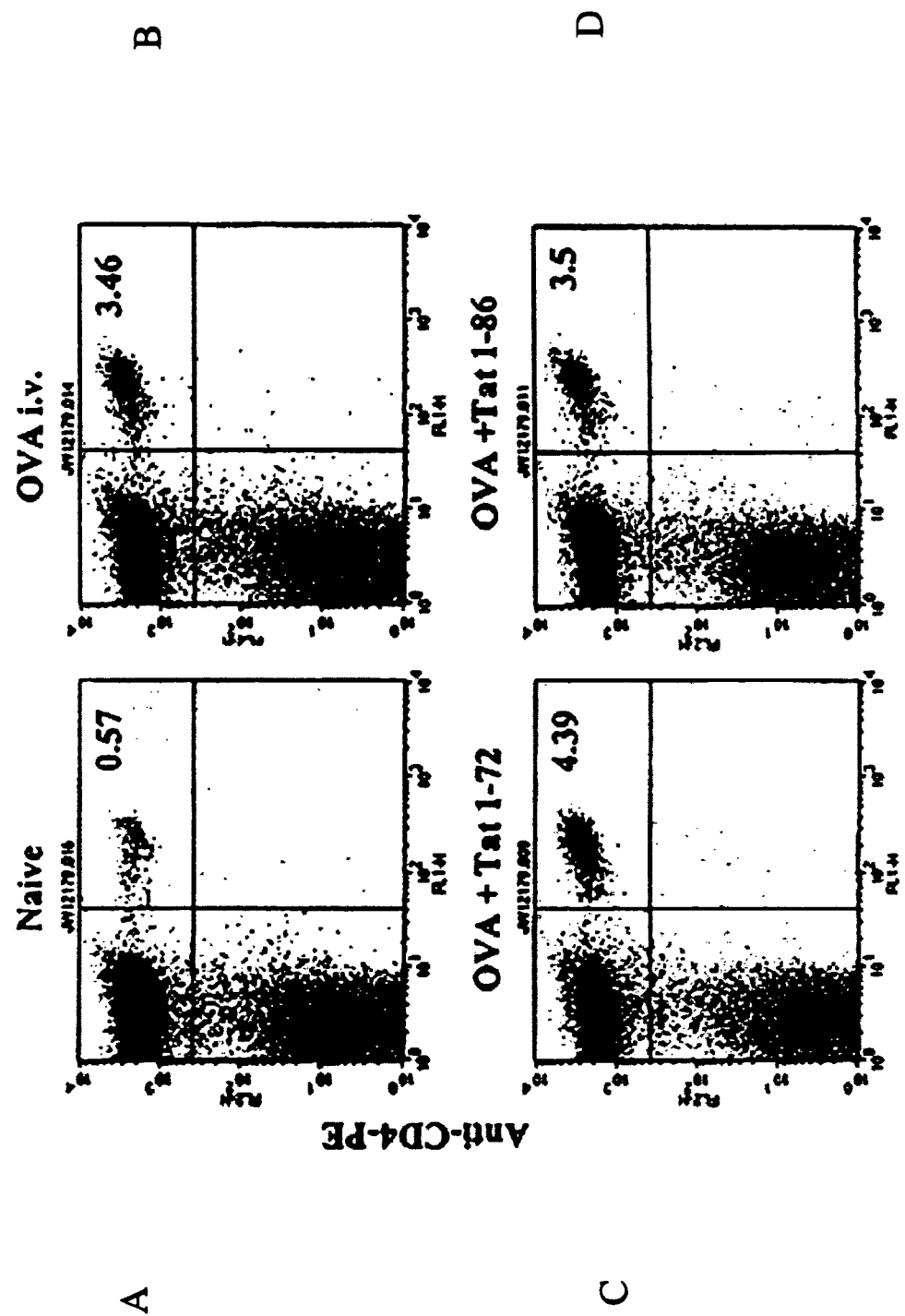
FIG. 5 depicts the results of the flow cytometry protocol outlined in Example 2. The numbers in the upper right quadrant represent the percent KJ1-26, CD4-cells. Shown are the results from a single mouse for each group. Two groups of mice were tested, and the results of the second group of animals (not shown) are identical to the results shown in FIG. 5.

The results are shown in FIG. 5. The numbers in the upper right hand quadrants represent the percentage of KJ1-26, CD4+ cells. Immunization with the OVA peptide alone induced in vivo clonal expansion of T cells. This result is represented by the 3.46% KJ-positive cells in the OVA mice (FIG. 5B) versus the 0.57% in the control group (FIG. 5A). The percentage KJ1-26 positive cells in the Tat 1-72 (FIG. 5C) and in the Tat 1-86 (FIG. 5D) were not significantly different from the cells of group B. This result indicates that neither Tat 1-72 nor Tat 1-86 did not suppress T cell proliferation in vivo.

Example 3

Preparation of Tat-Adsorbed Nanoparticles

The present example is provided to describe the preparation of Tat-adsorbed nanoparticles.

Nanoparticles were prepared as described above, having a particle size and zeta potential prior to protein binding of 105±11 nm and −65.1±2 mV, respectively, as shown on FIG. 6. Tat protein was adsorbed on the surface of the GPC purified anionic nanoparticles by gently mixing 25 µg/mL of Tat with 1 mL of GPC purified nanoparticles in 10% lactose. The Tat-adsorbed nanoparticles were then co-incubated with either phosphate-buffered saline (PBS, 10 mM, pH7.4), fetal bovine serum (10%, v/v) in normal saline, or 10% (w/v) lactose for 30 min at 37° C. The particle size stability was verified in several simulated biological media prior to incubation (white bars) and after incubation (black bars) as shown on FIG. 7.

Example 4

Tat-Adsorbed Nanoparticles Induces Enhanced Humoral and Cell Mediated Responses

The present example is provided to demonstrate the effectiveness of Tat-adsorbed nanoparticles.

(a) To determine the immunogenicity of Tat-adsorbed nanoparticles, mice were twice immunized with either Tat (5 µg) adjuvanted with Alum (15 µg, GlaxoSmithKline), Tat (5 µg) adsorbed on nanoparticles, or Tat (5 µg) adjuvanted with lipid A (50 µg) on day 0 and day 14. On day 28, the mice were sacrificed. Mice were harvested on day 28. A fourth group of naïve mice were untreated and used as negative control. The sera were diluted as indicated prior to ELISA.

Figure 8:
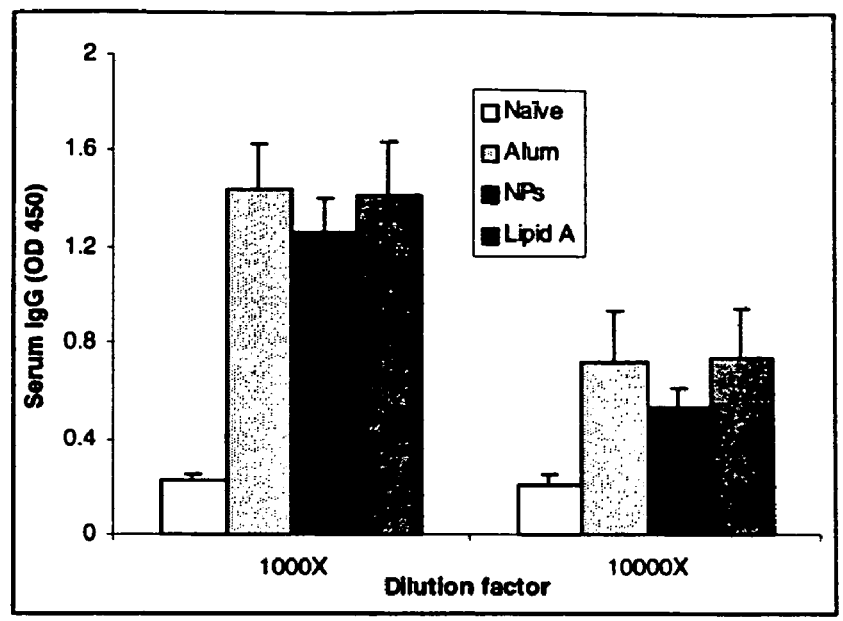
FIG. 8 shows Tat-specific serum IgG (A) and IgM (B) levels measured 28 days after the initial immunization of four groups of mice, (i) mice immunized with Tat adjuvanted with Alum (lighter shaded bars), (ii) mice immunized with Tat-adsorbed nanoparticles (NPs) (black bars), (iii) mice immunized with Tat adjuvanted to lipid A (darker shaded bars) and (iv) naïve mice (white bars) Naïve mice are indicated by the Data reported were mean±S. D. (n=5). * indicates that the results from the immunized mice were significantly different from that from the naïve mice, whereas there was no significant difference among the three immunized groups.
Figure 8:
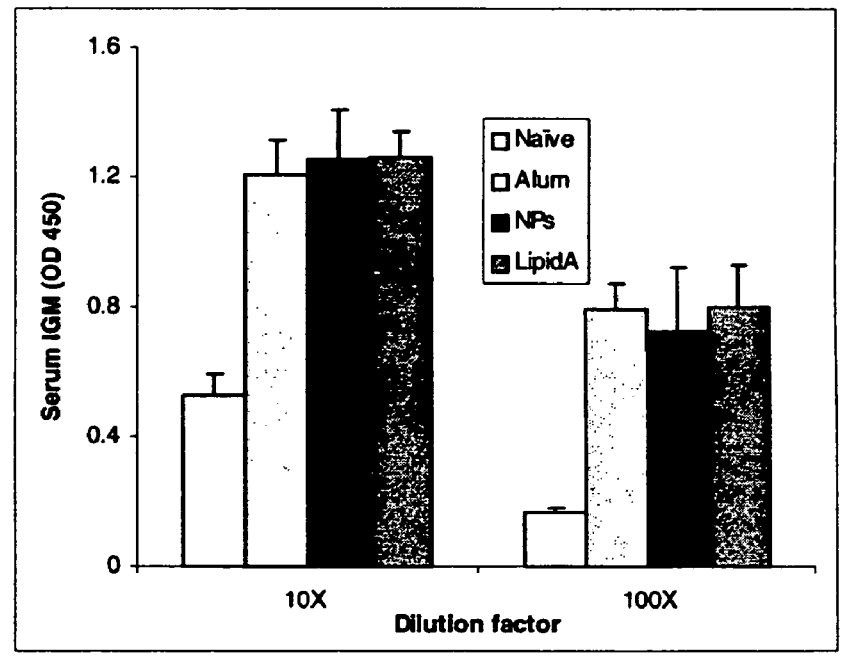

Shown in FIG. 8 are the Tat-specific antibody levels for IgG (FIG. 8A) and IgM. (FIG. 8B) in serum. The antibody responses were strong since even after 10,000-fold of dilution, the IgG titers from the immunized mice were still 2.3-3.0-fold greater than that from the naïve mice. Moreover, the antibody titers from mice immunized with the Tat-adsorbed nanoparticles were comparable to that from the mice immunized with Tat adjuvanted with Alum, a "gold" standard adjuvant for antibody induction. Statistical analyses (ANOVA) did not reveal any significant difference in both IgG and IgM among the three groups of immunized mice.

(b) To determine the cytokine profile of the proliferating T cells, mice were twice immunized with either Tat (5 µg) adjuvanted with Alum (15 µg, GlaxoSmithKline), Tat (5 µg) adsorbed on nanoparticles, or Tat (5 µg) adjuvanted with lipid A (50 µg) on day 0 and day 14. On day 28, the spleens were removed and splenocytes were prepared as described above. The isolated splenocytes, (1×10$^6$ cells/well) with three replicates (n=3) were seeded into a 48-well plate (Costar), and stimulated with 2 µg/well of Tat protein. After incubation with Tat (2 µg/5×10$^6$ cells) at 37° C. with 5% CO$_2$ for 48 hours, the splenocytes were spun down and the supernatant was collected and stored at −20° C. prior to further use. Naïve mice were untreated and used as negative control. Cytokine concentration (IFN-γ and IL-4) in the supernatants was determined using ELISA kits from Pierce-Endogen (Rockford, Ill.).

The results are shown in FIGS. 9 and 10. Strong and significant differences were observed for the in vitro cytokine release and proliferation of the isolated splenocytes among these three groups. The overall level of IL-4 release was low for all groups. More importantly, Alum as adjuvant led to the highest IL-4 release (FIG. 9B) and very weak IFN-γ release (FIG. 9A). Also, lipid A as adjuvant led to the highest IFN-γ release, an indication of Th1 immune responses (FIG. 9A). The nanoparticles adsorbed with Tat resulted in IFN-γ level similar to that from the lipid A adjuvanted Tat and 3.3-fold higher than that from the Alum adjuvanted Tat. This observation, combined with the fact that the IL-4 release from splenocytes isolated from mice immunized with the nanoparticles adsorbed with Tat was significantly lower than that from mice immunized with Alum adjuvanted Tat, strongly suggested that the Tat-adsorbed nanoparticles led to Th1 biased immune responses.

(c) To determine the ability of Tat-adsorbed nanoparticles to induce Tat-specific T-cell proliferation, mice were twice immunized with either Tat (5 μg) adjuvanted with Alum (15 μg, GlaxoSmithKline), Tat (5 μg) adsorbed on nanoparticles, or Tat (5 μg) adjuvanted with lipid A (50 μg) on day 0 and day 14. On day 28, the spleens were removed and splenocytes were prepared as described above. The isolated splenocytes ($1\times10^6$ cells/well) with three replicates (n=3) were seeded into a 48-well plate (Costar), and stimulated with Tat (0 or 2 μg/$5\times10^6$ cells). After incubation with Tat at 37° C. with 5% $CO_2$ for 96 hours, 60 μL of the combined MTS/PMS solution (Promega) was pipetted into each well (20 μL/100 μL of cells in medium). After an additional 4.5 hours of incubation at 37° C. with 5% $CO_2$, the absorbance at 490 nm was measured using a Universal Microplate Reader. The cell proliferation was reported as the % increase of the $OD_{490}$ of the stimulated cells (2 μg/well) over the $OD_{490}$ of un-stimulated cells (0 μg/well) (i.e., $100\times(OD490_{stimulated}-OD490_{un-stimulated})/OD490_{un-stimulated}$). Naïve mice were untreated and used as negative control.

As shown in FIG. 10. Tat-adsorbed nanoparticles also resulted in greater proliferation of isolated splenocytes than Tat adjuvanted with Alum, an indication of enhanced memory immune response from the nanoparticles. There was no difference between the Naïve and the Alum groups.

The foregoing illustrative examples are provided to demonstrate the principles of the invention, and are not intended to be limiting. One of skill in the art will recognize that additional embodiments are possible within the scope of the present invention, and the presentation of the foregoing examples is not meant to imply limitation of the invention to the examples.

All references cited herein, including patents, patent applications and non-patent literature references, are expressly incorporated herein by reference.

---

What is claimed is:

1. An immunogenic composition comprising Human Immunodeficiency Virus (HIV) Tat adsorbed to the surface of anionic nanoparticles, by electrostatic interactions,
   wherein said composition is capable of inducing strong humoral and cell-mediated anti-Tat responses.

2. The nanoparticle according to claim 1, wherein the Tat consists of amino acids 1-72 of wild-type Tat.

3. The nanoparticle according to claim 1, wherein the Tat consists of amino acids 1-86 of wild-type Tat.

4. The nanoparticle according to claim 1, wherein the Tat consists of mTat 1-86, wherein amino acid 22 is mutated to glycine.

5. An immunogenic composition comprising Human Immunodeficiency Virus (HIV) Tat-absorbed nanoparticles obtained by a process comprising the steps of:
   (a) producing a Tat protein according to the process comprising:
      (1) biosynthesizing Tat in a bacterial cell culture;
      (2) producing a crude isolate of Tat;
      (3) removing bacterial RNA from the crude isolate of Tat; and
      (4) isolating Tat protein from endotoxin in the crude isolate of step (3);
   (b) preparing purified anionic nanoparticles from microemulsion precursors; and
   (c) mixing the purified nanoparticles with the Tat protein from step (4),
      wherein said Tat is adsorbed to the surface of said nanoparticles through electrostatic interactions and said Tat-adsorbed nanoparticles are capable of inducing strong humoral and cell-mediated anti-Tat immune responses.

6. The Tat-adsorbed nanoparticles according to claim 5, wherein the step for biosynthesizing Tat in a bacterial cell culture comprises introducing DNA coding for a naturally biotinylated fusion protein of Tat into a bacterial cell culture, isolating from the bacterial cell culture a naturally biotinylated fusion protein of Tat by affinity chromatography on an avidin resin, and cleaving Tat from the fusion protein with factor Xa.

7. The Tat-adsorbed nanoparticles according to claim 6, wherein the step for biosynthesizing Tat in a bacterial cell culture further comprises eluting the cleaved Tat from the avidin resin.

8. The Tat-adsorbed nanoparticles according to claim 5, wherein the step for removing bacterial RNA from Tat comprises digesting the bacterial RNA in the presence of RNAse.

9. The Tat-adsorbed nanoparticles according to claim 5, wherein the step for isolating Tat from endotoxin comprises exposing Tat to a polymixin column to remove endotoxin.

10. The Tat-adsorbed nanoparticles according to claim 5, further comprising incubating the mixture of purified nanoparticles and Tat with phosphate-buffered saline, fetal bovine serum in normal saline, or lactose.

11. A process for producing an immunogenic composition comprising human immunodeficiency virus (HIV) Tat adsorbed to the surface of anionic nanoparticles by electrostatic interactions comprising the following steps:

(a) producing a Tat protein comprising the following steps:
(1) biosynthesizing Tat protein in a bacterial cell culture;
(2) producing a crude isolate of Tat;
(3) removing bacterial RNA from the crude isolate of Tat;
(4) isolating Tat protein from endotoxin in the crude isolate of step (3);
(b) mixing anionic nanoparticles with the Tat protein of step (4); and
(c) isolating and purifying said Tat-adsorbed anionic nanoparticles,
wherein said composition is capable of inducing strong humoral and cell-mediated anti-Tat responses.

12. The process according to claim 11, wherein the step for biosynthesizing a crude isolate of biosynthesizing Tat in a bacterial cell culture comprises introducing DNA coding for a naturally biotinylated fusion protein of Tat into a bacterial cell culture, isolating from the bacterial cell culture a naturally biotinylated fusion protein of Tat by affinity chromatography on an avidin resin, and cleaving Tat from the fusion protein with factor Xa.

13. The process according to claim 11, wherein the step for producing a crude isolate of Tat comprises eluting cleaved Tat from the avidin resin.

14. The process according to claim 11, wherein the step for removing bacterial RNA from Tat comprises digesting the bacterial RNA in the presence of RNAse.

15. The process according to claim 11, wherein the step for isolating Tat from endotoxin comprises exposing Tat to a polymixin column to remove endotoxin.

16. The process according to claim 11, further comprising incubating the mixture of purified nanoparticles and Tat with phosphate-buffered saline, fetal bovine serum in normal saline, or lactose.

17. A Tat-adsorbed nanoparticle delivery system for the delivery of protein antigens comprising the nanoparticles according to claim 1.

18. The process for producing the nanoparticles of claim 11, further comprising the step of preparing purified anionic nanoparticles from microemulsion precursor.

* * * * *